United States Patent
Kamei

(10) Patent No.: US 8,542,095 B2
(45) Date of Patent: Sep. 24, 2013

(54) BIOMETRIC AUTHENTICATION DEVICE, BIOMETRIC AUTHENTICATION METHOD, AND STORAGE MEDIUM

(75) Inventor: Toshio Kamei, Tokyo (JP)

(73) Assignee: NEC Corporation, Tokyo (JP)

( * ) Notice: Subject to any disclaimer, the term of this patent is extended or adjusted under 35 U.S.C. 154(b) by 438 days.

(21) Appl. No.: 12/918,720

(22) PCT Filed: Jan. 19, 2009

(86) PCT No.: PCT/JP2009/050644
§ 371 (c)(1), (2), (4) Date: Aug. 20, 2010

(87) PCT Pub. No.: WO2009/104437
PCT Pub. Date: Aug. 27, 2009

(65) Prior Publication Data
US 2010/0328033 A1  Dec. 30, 2010

(30) Foreign Application Priority Data
Feb. 22, 2008 (JP) ................... 2008-040882

(51) Int. Cl.
*G05B 19/00* (2006.01)
*G06K 9/00* (2006.01)

(52) U.S. Cl.
USPC ......... 340/5.82; 340/5.83; 382/124; 382/103; 382/115

(58) Field of Classification Search
USPC ............... 340/5.8, 5.82, 8.83; 382/124, 103, 382/115
See application file for complete search history.

(56) References Cited

U.S. PATENT DOCUMENTS

| | | | |
|---|---|---|---|
| 7,433,729 B2 * | 10/2008 | Setlak et al. | 600/473 |
| 2006/0286998 A1 * | 12/2006 | Fukuda | 455/550.1 |
| 2008/0227501 A1 * | 9/2008 | Joo et al. | 455/566 |
| 2008/0260211 A1 * | 10/2008 | Bennett et al. | 382/115 |
| 2010/0008545 A1 * | 1/2010 | Ueki et al. | 382/115 |
| 2010/0150452 A1 | 6/2010 | Kamei | |
| 2012/0218078 A1 * | 8/2012 | Hill | 340/5.82 |

FOREIGN PATENT DOCUMENTS

| | | |
|---|---|---|
| JP | 59-000778 A | 1/1984 |
| JP | 07-021373 A | 1/1995 |

(Continued)

OTHER PUBLICATIONS

A.H.M. Akkermans et al., "Acoustic Ear Recognition for Person Identification", Fourth IEEE Workshop on Automatic Identification Advanced Technologies, 2005, pp. 219-223.

(Continued)

*Primary Examiner* — George Bugg
*Assistant Examiner* — Munear Akki
(74) *Attorney, Agent, or Firm* — Sughrue Mion, PLLC

(57) ABSTRACT

Provided is a biometric authentication device that can enhance usability, suppress deterioration of authentication accuracy due to ambient noise, and increase tolerance to wiretapping. A biometric authentication device generates a signal pattern toward a living body by using a signal pattern generating means 11, and transmits the signal pattern to the living body in accordance with the signal pattern by a signal transmitting means 12. Further, the device receives a response signal transmitted through the living body by a signal receiving means 13. The device then calculates transfer feature in accordance with the signal pattern and the response signal by a transfer feature calculating means 14. Further, the device extracts and collates a feature amount in accordance with the transfer features.

15 Claims, 10 Drawing Sheets

(56) References Cited

FOREIGN PATENT DOCUMENTS

| | | |
|---|---|---|
| JP | 10-127609 A | 5/1998 |
| JP | 2002-136504 A | 5/2002 |
| JP | 2003-058190 A | 2/2003 |
| JP | 2003-187229 A | 7/2003 |
| JP | 2003-248664 A | 9/2003 |
| JP | 2007-113264 A | 5/2007 |
| JP | 2008-282084 A | 11/2008 |

OTHER PUBLICATIONS

Haruhiko Okumura et al., "Computer Algorithm Dictionary" Gijutsu-Hyohron Co., Ltd., 1987, pp. 133-134.

Japanese Standards Association, "Specification of Implementation for IC Cards—Part 4: High Speed Proximity Cards", Jul. 20, 2005, JISX6319-4.

* cited by examiner

BIOMETRIC AUTHENTICATION DEVICE, BIOMETRIC AUTHENTICATION METHOD, AND STORAGE MEDIUM

TECHNICAL FIELD

The present invention relates to a biometric authentication device, a biometric authentication method, and a storage medium, and more particularly, to a technique of performing personal identification using transfer feature information of a signal in a living body. The present invention also relates to a contact-type biometric authentication device, a biometric authentication method, and a storage medium having high reliability with which counterfeiting is difficult.

BACKGROUND ART

Examples of related biometric authentication devices are disclosed in a patent document 1, a patent document 2, and a non-patent document 1.

Biometric authentication systems of these types include, as shown in FIG. 3 of the patent document 1, an externally-supplied sound determination unit, an externally-supplied sound synthesizing unit, a bone conduction speaker, a bone conduction microphone, a feature amount extraction unit, a feature amount collation unit, and a feature amount database.

A biometric authentication system having such a configuration operates as follows. A biometric authentication system determines externally-supplied sound that is supplied from outside of a person to be authenticated by the externally-supplied sound determination unit, synthesizes the externally-supplied sound based on the determined externally-supplied sound, and transmits the synthesized sound to the bone conduction speaker. The signal transmitted from the bone conduction speaker is received by the bone conduction microphone through a human body (skeleton) of the person to be authenticated who contacts the system. The biometric authentication system extracts the personal feature by performing frequency analysis of the bone conduction sound in the feature extraction unit from the received signal, and performs collation with personal data which is enrolled in the feature amount database by the feature amount collation unit, so as to perform personal authentication.

Further, a biometric authentication device disclosed in the patent document 2 includes a pulse generation unit, a speaker, a data synthesis unit, a microphone, a template storing unit, and a comparative determination processing unit. The pulse generation unit generates a pulse, and irradiates a finger of the person to be authenticated contacted to the speaker with a signal that is amplified by an amplifier. The biometric authentication device receives an impulse signal transmitted through living body tissue of the finger by the microphone. The data synthesis unit synthesizes the pulse generated by the pulse generation unit and the impulse received by the microphone. The biometric authentication device stores synthesized synthetic wave in the template storing unit as personal identification information of the person to be authenticated. The biometric authentication device generates a synthetic wave in authentication in the same way as enrollment, calculates the mean square value of the difference of the template by the comparative determination processing unit, and performs personal identification processing by the threshold processing of the mean square value.

Meanwhile, the non-patent document 1 suggests a method of carrying out biometric authentication using an ear canal (earhole). This method observes a response signal of an acoustic signal transmitted to the ear canal with a speaker by a microphone that does not directly contact to the living body, and obtains a transfer function of a signal in the ear canal by Fourier transformation from the acoustic signal and the response signal. In this method, personal identification is performed using linear discriminant analysis for this transfer function.

[Patent document 1]
Japanese Unexamined Patent Application Publication No. 2003-58190
[Patent document 2]
Japanese Unexamined Patent Application Publication No. 2003-248664
[Non-patent document 1]
A. H. M. Akkermans, T. A. M. Kevenaar, D. W. E. Schobben, titled "Acoustic Ear Recognition for Personal Identification", (U.S.A), Fourth IEEE Workshop on Automatic Identification Advanced Technologies (AutoID'05)), 2005, p. 219-223

DISCLOSURE OF INVENTION

Technical Problem

As described above, the biometric authentication device using the method disclosed in the non-patent document 1 transmits the acoustic signal employing air as a medium to the ear canal. Hence, the problem is that the acoustic signal is susceptible to sound (noise) of external environment. Further, a part to which the biometric authentication device is attached is limited to a part around an ear. Thus it is not necessarily have high usability.

The non-contact-type biometric authentication device using the acoustic signal disclosed in the non-patent document 1 performs personal identification using the acoustic echo reflected from the living body. The information to identify the personality is the acoustic echo that reflects the shape of the ear canal. Hence, noise from external environment is the noise component, which may cause degradation of accuracy of authentication. Further, a body part with cavity is a part from which the acoustic echo can be easily obtained due to its low susceptibility to noise. This part is limited to an oral cavity or a nasal cavity, other than the ear canal. However, the oral cavity and the nasal cavity are covered with mucous membrane, and neither of them is suitable as a part to which artifacts such as a microphone and a speaker are attached. Further, a user may feel visually uncomfortable attaching artifacts to those parts. Meanwhile, the device may be attached to an ear when information of an ear canal is used. In order to control the device attached to the ear, a user needs to manipulate the device with his/her hand using a control device connected with a wire or wirelessly, which makes the device complicated. As stated above, the problem is the low (degraded) usability due to the low freedom of design in the device.

Further, a method disclosed in the patent document 1 or the patent document 2 extracts features or creates templates using a signal transmitted and received from a living body by a bone conduction microphone and the like. Hence, if the bone conduction sound can be wiretapped and the wiretapping sound can be reproduced for a biometric authentication device, it is possible to mislead the biometric authentication device to allow the authentication device to improperly perform authentication operation in principle. Therefore, the problem is the low reliability against wiretapping, which means low tolerance to false authentication.

Accordingly, one object of the present invention is to provide a biometric authentication device that is capable of solving afore-mentioned problems of "low usability, low accuracy of authentication due to ambient noise, and low tolerance to wiretapping".

Technical Solution

In order to achieve the objects stated above, a biometric authentication device according to one aspect of the present invention includes a signal pattern generating means that generates a signal pattern of a signal transmitted to a living body, a signal transmitting means that transmits a signal to the living body based on the signal pattern from the signal pattern generating means, a signal receiving means that receives a response signal transmitted from the living body, a transfer feature calculating means that calculates a transfer feature of a signal transmitted through the living body based on the signal pattern from the signal pattern generating means and the response signal received by the signal receiving means, a feature amount extracting means that extracts a feature amount based on the transfer feature that is calculated, the feature amount varying for every living body, and a feature amount collating means that collates the extracted feature amount with a feature amount stored in a feature amount storing means in advance.

Further, a biometric authentication method according to another aspect of the present invention includes a signal pattern generating process that generates a signal pattern of a signal transmitted to a living body, a signal transmitting process that transmits a signal to the living body based on the signal pattern generated by the signal pattern generating process, a signal receiving process that receives a response signal transmitted from the living body, a transfer feature calculating process that calculates a transfer feature of a signal transmitted through the living body based on the signal pattern generated by the signal pattern generating process and the response signal received by the signal receiving process, a feature extracting process that extracts a feature amount based on the transfer feature that is calculated, the feature amount varying for every living body, and a feature amount collating process that collates the extracted feature amount with a feature amount stored in a feature amount storing means in advance.

Furthermore, a biometric authentication program according to another aspect of the present invention makes a biometric authentication device including a signal transmitting means that transmits a signal to a living body and a signal receiving means that receives a response signal transmitted through the living body to perform biometric authentication based on the response signal achieve the following a signal pattern generating means that generates a signal pattern of a signal transmitted to the living body and outputs the signal pattern that is generated to the signal transmitting means, a transfer feature calculating means that calculates a transfer feature of a signal transmitted through the living body based on the signal pattern from the signal pattern generating means and the response signal received by the signal receiving means, a feature amount extracting means that extracts a feature amount based on the transfer feature that is calculated, the feature amount varying for every living body, and a feature amount collating means that collates the extracted feature amount with a feature amount stored in a feature amount storing means in advance.

Advantageous Effects

The present invention is configured as described above, thereby enhancing usability, suppressing deterioration of authentication accuracy due to ambient noise, and enhancing tolerance to wiretapping.

EXPLANATION OF REFERENCE

Figure 1:
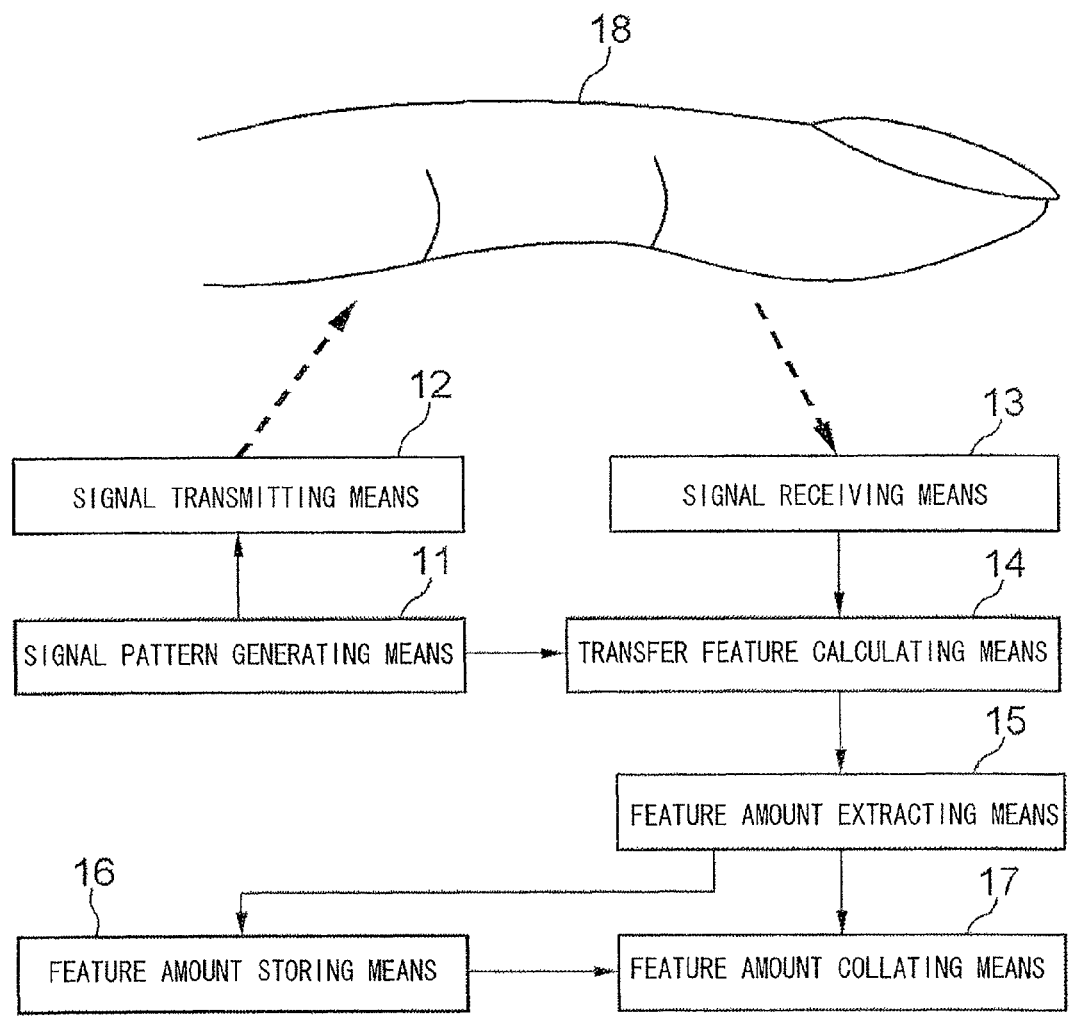
FIG. 1 is a block diagram showing a configuration of a biometric authentication device according to a first exemplary embodiment.

11 SIGNAL PATTERN GENERATING MEANS
12 SIGNAL TRANSMITTING MEANS
13 SIGNAL RECEIVING MEANS
14 TRANSFER FEATURE CALCULATING MEANS
15 FEATURE AMOUNT EXTRACTING MEANS
16 FEATURE AMOUNT STORING MEANS

17 FEATURE AMOUNT COLLATING MEANS
18 LIVING BODY PART
31 CLOCK MEANS
32 NORMAL RANDOM NUMBER GENERATING MEANS
41 FIRST FOURIER TRANSFORMING MEANS
42 SECOND FOURIER TRANSFORMING MEANS
43 TRANSFER FUNCTION CALCULATING MEANS
51 VECTOR PROJECTION MEANS
52 BASIS MATRIX STORING MEANS
53 MEAN VECTOR STORING MEANS
65 LIGHT SOURCE
66 CAMERA
71 SIGNAL TRANSMITTING MEANS
72 SIGNAL RECEIVING MEANS
73 SIGNAL PATTERN COLLATION UNIT
74 ILLUMINATION MEANS
75 IMAGING MEANS
76 FINGER PATTERN COLLATION UNIT
77 COLLATION INTEGRATION UNIT
81 PORTABLE TELEPHONE
83 BONE CONDUCTION MICROPHONE
111 BONE CONDUCTION SPEAKER
112 BONE CONDUCTION MICROPHONE
113 IC
114 ANTENNA

BEST MODE FOR CARRYING OUT THE INVENTION

A biometric authentication device according to one aspect of the present invention is a device that performs biometric authentication by transmitting a signal to a living body and receiving a response signal that is transmitted through the living body.

This biometric authentication device includes a signal pattern generating means that generates a signal pattern of a signal transmitted to a living body, a signal transmitting means that transmits a signal to the living body based on the signal pattern from the signal pattern generating means, a signal receiving means that receives a response signal transmitted from the living body, a transfer feature calculating means that calculates a transfer feature of a signal transmitted through the living body based on the signal pattern from the signal pattern generating means and the response signal received by the signal receiving means, a feature amount extracting means that extracts a feature amount based on the transfer feature that is calculated, the feature amount varying for every living body, and a feature amount collating means that collates the extracted feature amount with a feature amount stored in a feature amount storing means in advance.

Accordingly, the device transmits a signal to a living body and measures a response signal that is transmitted through the living body, whereby the device is hardly influenced by sound (ambient noise) of external environment. Therefore, deterioration of authentication accuracy due to ambient noise can be suppressed.

Further, according to the configuration as above, the biometric authentication can be performed based on the response signal that transmits through a part such as a finger, a hand, or a head. Therefore, the freedom of the living body part to which the biometric authentication device can be applied can be 3 0 increased (expanded), and the freedom of design of the biometric authentication device can be increased. In short, usability of the biometric authentication device can be enhanced.

In addition, according to the configuration as above, the biometric authentication is performed based on the signal pattern of the signal that is transmitted, and the response signal that is received. Hence, even when the biometric authentication device is configured to change the signal pattern that is to be generated, the biometric authentication can be performed with high accuracy. Furthermore, in this case, it is possible to prevent false authentication operation that is caused by the response signal being wiretapped and the wiretapping sound being reproduced for the biometric authentication device. Hence, tolerance to wiretapping can be enhanced.

Furthermore, according to the configuration as above, the feature amount is extracted based on the transfer feature that is calculated. Therefore, the feature amount can be obtained with high accuracy. As a result, the biometric authentication can be performed with high accuracy.

In this case, it is preferable that the signal transmitting means is configured to transmit the signal to the living body while being contacted to the living body, and the signal receiving means is configured to receive the response signal from the living body while being contacted to the living body.

Further, in this case, it is preferable that the signal transmitting means is configured to transmit the signal through a bone conduction-type speaker, the signal receiving means is configured to receive the response signal through a bone conduction-type microphone, and the transfer feature is an acoustic transfer function in the living body.

Furthermore, according to another aspect of the biometric authentication device of the present invention, it is preferable that the signal transmitting means is configured to transmit the signal through an electrode, the signal receiving means is configured to receive the response signal through an electrode, and the transfer feature is an electrical transfer function in the living body.

On the other hand, in any of the biometric authentication device, the signal pattern generating means is preferably configured to change the signal pattern every time the signal pattern generating means generates the signal pattern.

Accordingly, it is possible to prevent false authentication operation that is caused by the response signal being wiretapped and the wiretapping sound being reproduced for the biometric authentication device. Hence, tolerance to wiretapping can be enhanced.

In this case, the signal pattern generating means is preferably configured to generate a signal pattern indicating white noise as the signal pattern.

Further, in this case, the feature amount collating means is preferably configured to perform the collation by performing comparison processing based on a feature amount that is stored in a feature amount storing means in advance and the feature amount that is extracted.

Further, in this case, it is preferable that the signal transmitting means is configured to transmit the signal to a part of a finger in the living body, the signal receiving means is configured to receive the response signal from the part of the finger in the living body, and the transfer feature is a transfer feature of the part of the finger.

Further, in this case, the biometric authentication device includes a finger pattern authenticating means that receives a pattern of a finger and collates an amount that indicates the input pattern of the finger with an amount that indicates a pattern of a finger that is stored in advance, in which the biometric authentication device is preferably configured to perform the biometric authentication based on a collation result by the feature amount collating means and a collation result by the finger pattern authenticating means.

Accordingly, the multimodal authentication can be performed, thereby achieving authentication with excellent tolerance to counterfeiting and authentication with high accuracy in which false rejection is greatly reduced.

Meanwhile, a portable telephone that includes any of the biometric authentication devices described above includes a control unit including a control unit that sets a state of the portable telephone to a state in which at least one function of the portable telephone can be used or a state in which at least one function of the portable telephone cannot be used based on the biometric authentication by the biometric authentication device.

In this case, the function includes a function that uses a non-contact-type IC.

Further, another biometric authentication device according to the present invention is a device that performs biometric authentication by transmitting a signal to a living body and receiving a response signal that is transmitted through the living body.

This biometric authentication device includes a signal pattern generating means that generates a signal pattern of a signal transmitted to the living body and outputs the generated signal pattern to a signal transmitting means, a transfer feature calculating means that calculates a transfer feature of a signal transmitted through the living body based on the signal pattern from the signal pattern generating means and a response signal received by a signal receiving means, a feature amount extracting means that extracts a feature amount effective for the biometric authentication based on the transfer feature that is calculated, and a feature amount collating means that collates the extracted feature amount with a feature amount stored in a feature amount storing means in advance.

Further, a biometric authentication method according to another aspect of the present invention is a method to perform biometric authentication by transmitting a signal to a living body and receiving a response signal transmitted through the living body.

This biometric authentication method includes a signal pattern generating process that generates a signal pattern of a signal transmitted to a living body, a signal transmitting process that transmits a signal to the living body based on the signal pattern generated by the signal pattern generating process, a signal receiving process that receives a response signal transmitted from the living body, a transfer feature calculating process that calculates a transfer feature of a signal transmitted through the living body based on the signal pattern generated by the signal pattern generating process and the response signal received by the signal receiving process, a feature extracting means that extracts a feature amount based on the transfer feature that is calculated, the feature amount varying for every living body, and a feature amount collating process that collates the extracted feature amount with a feature amount stored in a feature amount storing means in advance.

In this case, it is preferable that the signal transmitting process is configured to transmit the signal to the living body while being contacted to the living body, and the signal receiving process is configured to receive the response signal from the living body while being contacted to the living body.

Further, in this case, the signal transmitting process is configured to transmit the signal through a bone conduction-type speaker, the signal receiving process is configured to receive the response signal through a bone conduction-type microphone, and the transfer feature is an acoustic transfer function in the living body.

Further, according to another aspect of the biometric authentication method of the present invention, it is preferable that the signal transmitting process is configured to transmit the signal through an electrode, the signal receiving process is configured to receive the response signal through an electrode, and the transfer feature is an electrical transfer function in the living body.

Further, in any of the biometric authentication method, the signal pattern generating process is preferably configured to change the signal pattern every time the signal pattern is generated.

Further, in this case, the signal pattern generating process is configured to generate a signal pattern indicating white noise as the signal pattern.

A biometric authentication program according to another aspect of the present invention is a program making a biometric authentication device including a signal transmitting means that transmits a signal to a living body and a signal receiving means that receives a response signal transmitted through the living body to perform biometric authentication based on the response signal achieve the following: a signal pattern generating means that generates a signal pattern of a signal transmitted to the living body and outputs the signal pattern that is generated to the signal transmitting means; a transfer feature calculating means that calculates a transfer feature of a signal transmitted through the living body based on the signal pattern from the signal pattern generating means and the response signal received by the signal receiving means; a feature amount extracting means that extracts a feature amount based on the transfer feature that is calculated, the feature amount varying for every living body; and a feature amount collating means that collates the extracted feature amount with a feature amount stored in a feature amount storing means in advance.

Even the invention of the portable telephone, the biometric authentication method, or the biometric authentication program having the configuration stated above achieves the similar effect as the biometric authentication device, thereby achieving the object of the present invention stated above.

Hereinafter, exemplary embodiments of a biometric authentication device, a portable telephone, and a biometric authentication program according to the present invention will be described with reference to FIGS. 1 to 12.

<First Exemplary Embodiment>
(Bone Conduction Biometrics)

Next, best mode for carrying out the present invention will be described in detail with reference to the drawings. A biometric authentication device according to a first exemplary embodiment is applied to a finger as a biometric authentication part, and uses an acoustic signal that is typically called bone conduction sound.

Referring to FIG. 1, the biometric authentication device according to the first exemplary embodiment of the present invention includes a signal pattern generating means (signal pattern generating process) 11 that determines a signal pattern of a signal transmitted to a living body, a signal transmitting means (signal transmitting process) 12 including a contact-type device that amplifies the signal pattern obtained by the signal pattern generating means 11 and transmits the signal to a living body part 18 while being contacted to the living body part 18 which is the target, a signal receiving means (signal receiving process) 13 that receives a signal transmitted from the living body (response signal, reception signal) while being contacted to the living body part 18, a transfer feature calculating means (transfer feature calculating process) 14 that calculates (estimates) a transfer feature of a signal transmitted through the living body based on the signal pattern from the signal pattern generating means 11 and the reception signal from the signal receiving means 13, a feature amount extracting means (feature amount extracting process) 15 that extracts a feature amount from the transfer feature that is calculated (obtained), the feature amount being the amount effective for the biometric authentication and being varied for every living body, a feature amount storing means 16 that stores a feature amount for enrollment in advance, and a feature amount collating means (feature amount collating process) 17 that collates the feature amount that is received and the feature amount for enrollment stored in the feature amount storing means 16.

Figure 2A:
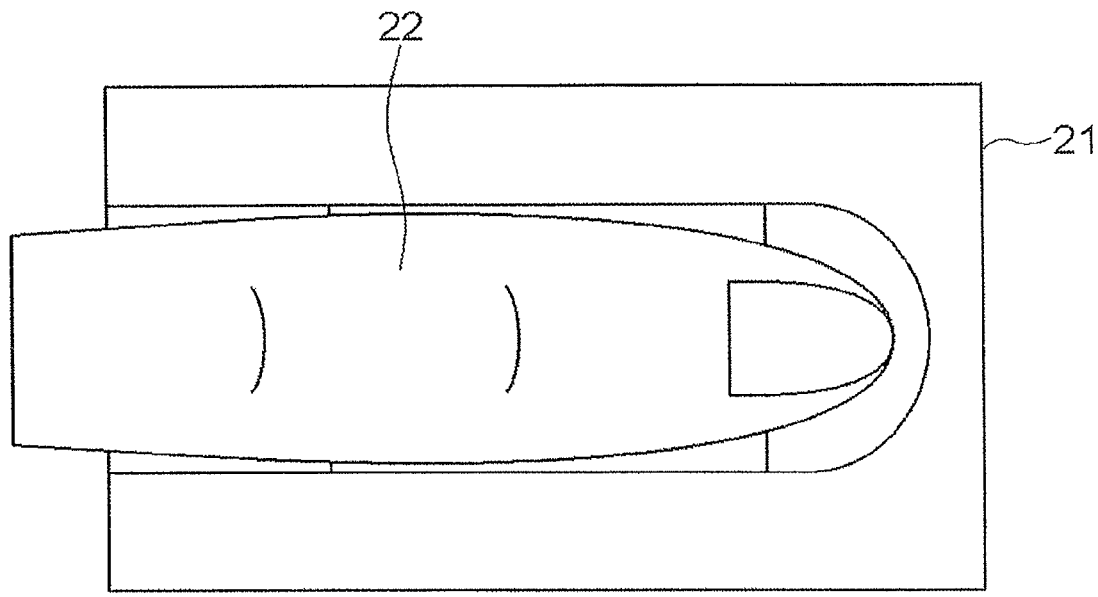
FIG. 2A is a diagram for describing a sensing unit of the biometric authentication device according to the first exemplary embodiment.
Figure 2B:
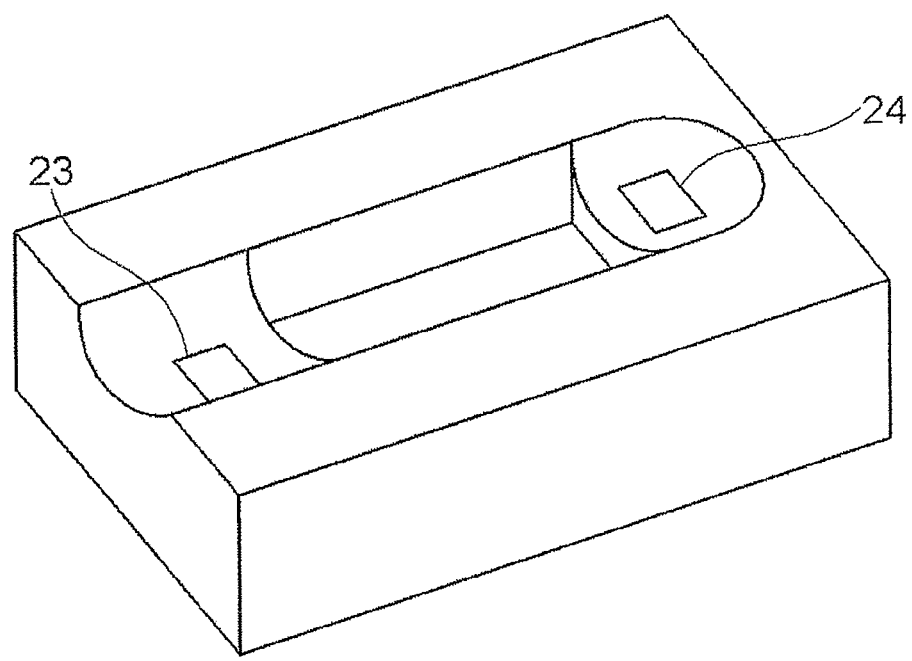
FIG. 2B is a diagram for describing the sensing unit of the biometric authentication device according to the first exemplary embodiment.

FIGS. 2A and 2B each show an external view of a sensing unit thereof. The signal transmitting means 12 is arranged, as shown in FIGS. 2A and 2B, substantially at a location 23 that corresponds to the proximal finger portion of a finger 22. The signal receiving means 13 is arranged at a location 24 that corresponds to the distal finger portion of the finger 22. According to such a configuration, signals are transmitted from the proximal finger portion to the distal finger portion of the finger.

The signal pattern generating means 11 generates a signal pattern s(t) to calculate the transfer feature. In this example, a signal pattern indicating white noise is used. The white noise means a signal that oscillates irregularly, and the Fourier power spectrum of the signal ideally has the same intensity for all frequencies.

By using white noise, a signal pattern having no deviation of frequency can be used as an input signal, thereby reducing variations of an estimation error by the frequency of the transfer function. As a result, transfer features can be calculated with higher accuracy.

As white noise, for example, normal random number (white Gaussian noise) or random number of Cauchy distribution (Cauchy noise) may be used, and a method of generating the white noise is disclosed in a non-patent document 2. When a digital signal is used, the random number sequence is always the same unless the seeds of the random number are not randomized. Thus, it is desired to randomize the seeds using time information or the like.

[Non-patent document 2]
Haruhiko Okumura, titled "Computer Algorithm Dictionary", Gijutsu-Hyohron Co., Ltd., 1987, p. 133-134

Figure 3:
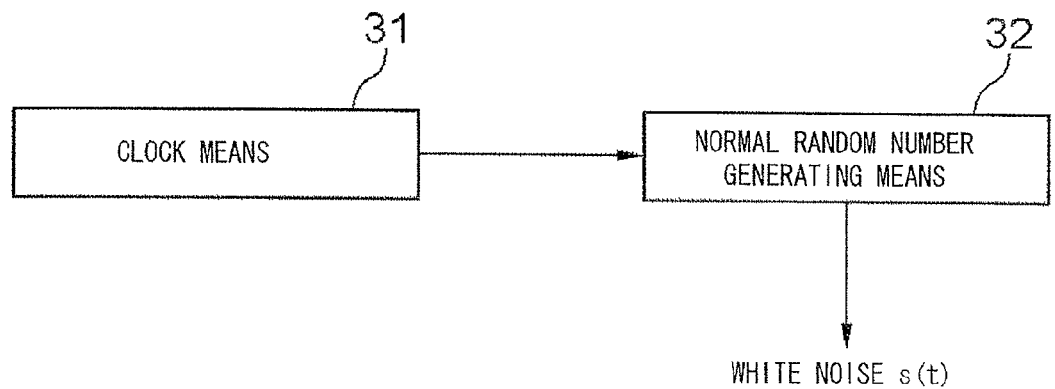
FIG. 3 is a diagram for describing a configuration of a signal pattern generating means according to the first exemplary embodiment.

FIG. 3 is a block diagram of the signal pattern generating means 11 configured to randomize the seeds using time information. The signal pattern generating means 11 includes a clock means 31 and a normal random number generating means 32.

The clock means 31 generates a random number (clock random number) based on the time information. The normal random number generating means 32 creates seeds based on the clock random number, and generates the normal random number sequence from the seeds with 20 kHz, so as to generate a signal pattern indicating the white Gaussian noise.

According to such a configuration, the signal pattern generating means 11 changes the signal pattern every time the signal pattern is generated.

Note that the seeds are not necessarily created every time the signal pattern is generated while it is guaranteed that the same sequence of the normal random number is not generated (while the device is started up); for example, the seeds may be updated when the device is started up.

The signal transmitting means 12 D-A converts (digital/analog converts) the white noise signal output from the signal pattern generating means 11 and amplifies the converted signal using an amplifier. The signal transmitting means 12 transmits the amplified signal to the proximal finger portion of the finger through a bone conduction-type speaker (bone conduction speaker). By using the bone conduction speaker, the signal (acoustic signal) is input to the finger from the proximal finger portion that contacts with the speaker. The acoustic signal is then transmitted through texture and bone of the finger.

The signal receiving means 13 includes a bone conduction-type microphone (bone conduction microphone). The signal receiving means 13 receives the bone conduction-type sound from the distal finger portion of the finger that contacts with the microphone and A/D converts (analog/digital converts) the received sound. In this specification, this signal is also called response signal r(t).

The transfer feature calculating means 14 calculates a transfer function $H(\omega)$ as a transfer feature based on the signal pattern s(t) generated by the signal pattern generating means 11 and the response signal r(t) received (obtained) by the signal receiving means 13.

When Fourier spectrum of s(t) is denoted by $S(\omega)$ and Fourier spectrum of r(t) is denoted by $R(\omega)$, transfer function $H(\omega)$ can be expressed by the following expression (1) using $S(\omega)$ and $R(\omega)$. Specifically, it is understood that transfer function $H(\omega)$ is the function that indicates the relation between the signal input from the bone conduction speaker to the living body (input signal) and the signal output to the bone conduction microphone (output signal, response signal) as a result of the input signal transmitting through the living body by bone conduction.

$$H(\omega) = \frac{R(\omega)}{S(\omega)} \qquad (1)$$

Figure 4:
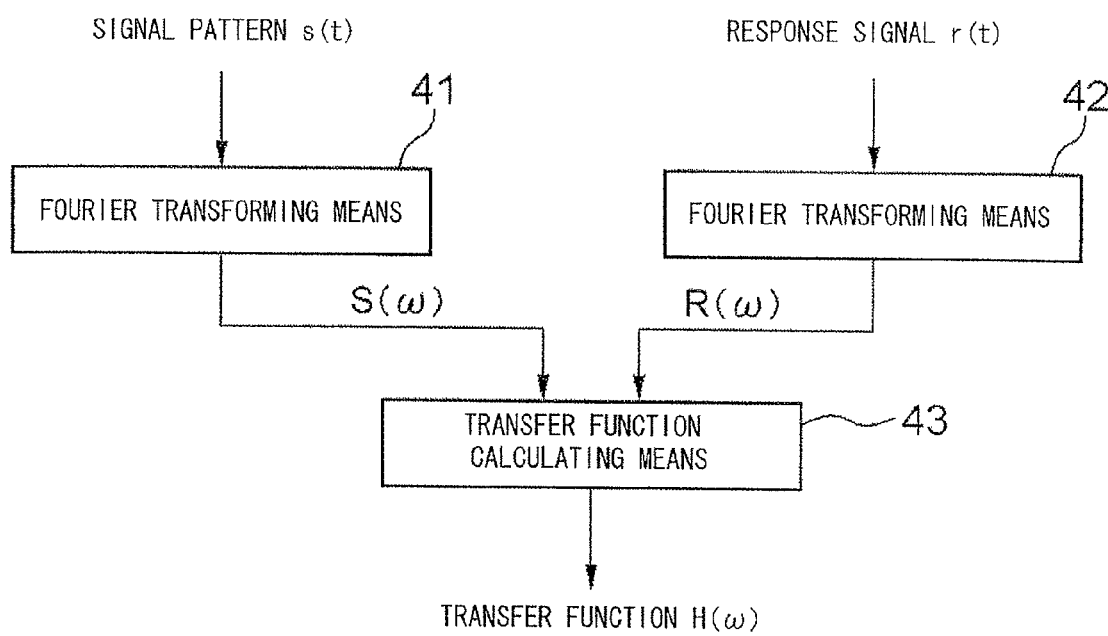
FIG. 4 is a diagram for describing a configuration of a transfer feature calculating means according to the first exemplary embodiment.

Hence, the transfer feature calculating means 14 includes, as shown in FIG. 4, a first Fourier transforming means 41 that calculates Fourier spectrum $S(\omega)$ by performing Fourier transformation on the signal pattern s(t), a second Fourier transforming means 42 that calculates Fourier spectrum $R(\omega)$ by performing Fourier transformation on the response signal r(t), and a transfer function calculating means 43 that calculates transfer function $H(\omega)$ based on the Fourier spectra $S(\omega)$ and $R(\omega)$ that are calculated above and the above expression (1).

The feature amount extracting means 15 extracts the feature amount based on the transfer function $H(\omega)$ that is calculated (obtained) by the transfer feature calculating means 14.

Figure 5:
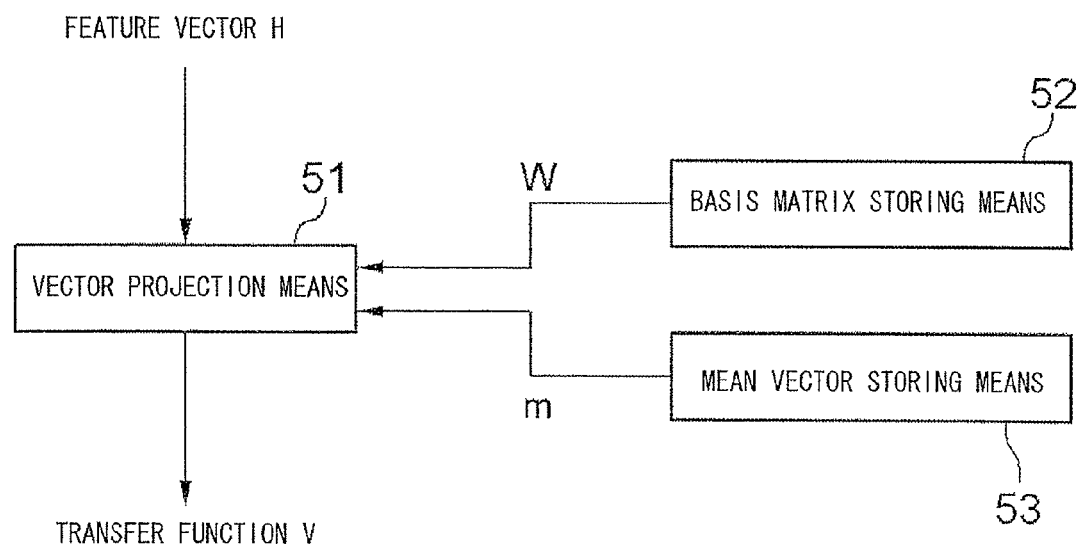
FIG. 5 is a diagram for describing a configuration of a feature amount extracting means according to the first exemplary embodiment.

For example, the feature amount may be extracted by using procedures such as principal component analysis or discriminant analysis. In this example, description will be made of a case in which the feature amount extracting means 15 is implemented with the discriminant analysis as an example. The feature amount extracting means 15 includes, as shown in FIG. 5, a vector projection means 51 that projects transfer function $H(\omega)$, a basis matrix storing means 52 that stores basis matrix W used for calculation in the vector projection means 51, and a mean vector storing means 53 that stores mean vector m.

The vector projection means 51 projects vector H on an M-dimensional space which is formed by the column vector of M basis matrices that satisfy M □ N using basis matrix W and mean vector m. Vector H has, as an element, each value of transfer function $H(\omega)$ that is received. This can be expressed by the following expression (2).

$$H = \begin{pmatrix} H(0) \\ H(1) \\ \vdots \\ H(N-1) \end{pmatrix} \quad (2)$$

$$v = w^T(H-m)$$

N represents number of elements of H(ω), W represents N×M-dimensional matrix, and m represents N-dimensional vector. The vector projection means 51 outputs M-dimensional feature vector v that is obtained as a feature amount.

The basis matrix storing means 52 calculates discriminant matrix by performing discriminant analysis in advance using a training set of vector H of the transfer function to perform personal identification, extracts M column vectors in order of decreasing specific values in the discriminant analysis, and stores the extracted vector as basis matrix W.

The mean vector storing means 53 calculates the mean vector using the training set in advance and stores the mean vector.

While the example using the discriminant analysis has been described above, a principal component matrix or a matrix indicating an independent component may be calculated using a procedure such as principal component analysis or independent component analysis instead of using discriminant analysis, so as to calculate basis matrix W.

In the biometric authentication processing, collation processing is performed by carrying out comparison processing based on the data which is registered in advance (enrolled data) and the data which is newly input (query data).

The feature amount storing means 16 stores feature vector v that is extracted by the feature amount extracting means 15 as enrolled data venroll for the enrollment operation. The feature amount storing means 16 provides venroll for the feature amount collating means 17 as enrolled data for the collation operation.

The feature amount collating means 17 collates two data by performing comparison processing between venroll stored in the feature amount storing means 16 and query data vquery newly obtained by a user putting a finger for the collation operation, so as to perform collation between two data. The query data vquery is extracted by extracting features of the data input for collation in the same way as the enrollment data venroll.

The comparison processing calculates the distance value between the two patterns and performs threshold processing on the distance value, so as to determine whether both are matched (match or mismatch).

The distance value d between the two patterns (venroll, vquery) is calculated according to the following expression (3) using the discriminant distance disclosed in Japanese Patent No. 3903783 by the inventor of the present invention.
[Patent document 3]
Japanese Patent No. 3903783

$$d(v_{enroll}, v_{query}) = (v_{enroll} - v_{query})^T (\Sigma_W^{-1} - \Sigma_B^{-1})(v_{enroll} - v_{query}) \quad (3)$$

Now, ΣW and ΣB are covariance matrix of a within-class distribution and covariance matrix of a between-class distribution of the feature vector v calculated using the training set that is prepared in advance. Further, the distance value may be calculated by the following expression (4) using σW,k and σB,k that are diagonal elements of ΣW and ΣB.

$$d(v_{enroll}, v_{query}) = \sum_{k=0}^{M-1} \left( \frac{1}{\sigma_{W,k}^2} - \frac{1}{\sigma_{B,k}^2} \right)(v_{enroll,k} - v_{query,k})^2 \quad (4)$$

Now, venroll,k and vquery,k are k-th elements of the feature vectors venroll and vquery, respectively.

This calculation is equivalent to the calculation in the expression (3) when the independence between the elements of v can be assumed. By performing such a calculation, the calculation amount can be decreased from the calculation amount of sum of products of the order of $M^2$ to the calculation amount of sum of products of the order of M, whereby high-speed calculation can be executed.

In this way, biometric authentication is performed by transmitting a signal to a living body and receiving a response signal transmitted via the living body, thereby enhancing usability, suppressing deterioration of authentication accuracy due to ambient noise, and enhancing tolerance to wiretapping.

In the first exemplary embodiment, the signal transmitting means transmits the signal through a bone conduction-type speaker, the signal receiving means receives the response signal through the bone conduction-type microphone, and the acoustic transfer function in the living body is used as the transfer feature. However, the signal transmitting means may transmit the signal through an electrode, the signal receiving means receives the response signal through the electrode, and an electrical transfer function in the living body may be used as the transfer feature. In this case, the signal is indicated by change in potential. Accordingly, the biometric authentication device can be manufactured with lower cost compared with the case of using the bone conduction speaker and the bone conduction microphone.

<Second Exemplary Embodiment>
(Multimodality With Finger Pattern Collation)

A biometric authentication device according to a second exemplary embodiment is a device that integrates authentications of two modals of an authentication of a finger based on a transfer feature and an authentication of a finger based on a pattern of a finger such as blood vessels or skin surface patterns, so as to achieve biometric authentication with enhanced accuracy and enhanced tolerance to a fake finger (false finger).

Figure 6A:
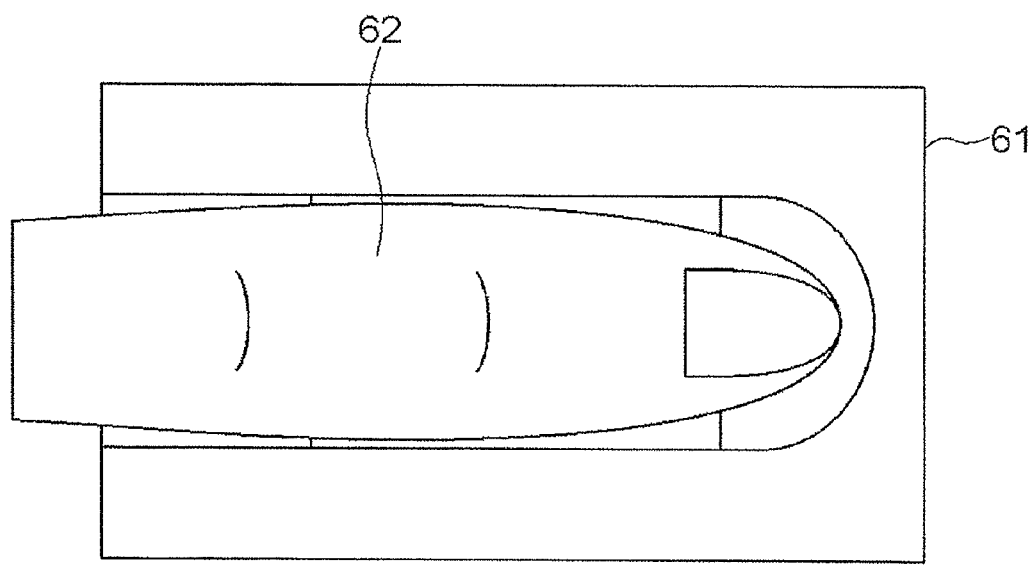
FIG. 6A is a diagram for describing a sensing unit of a biometric authentication device according to a second exemplary embodiment.
Figure 6B:
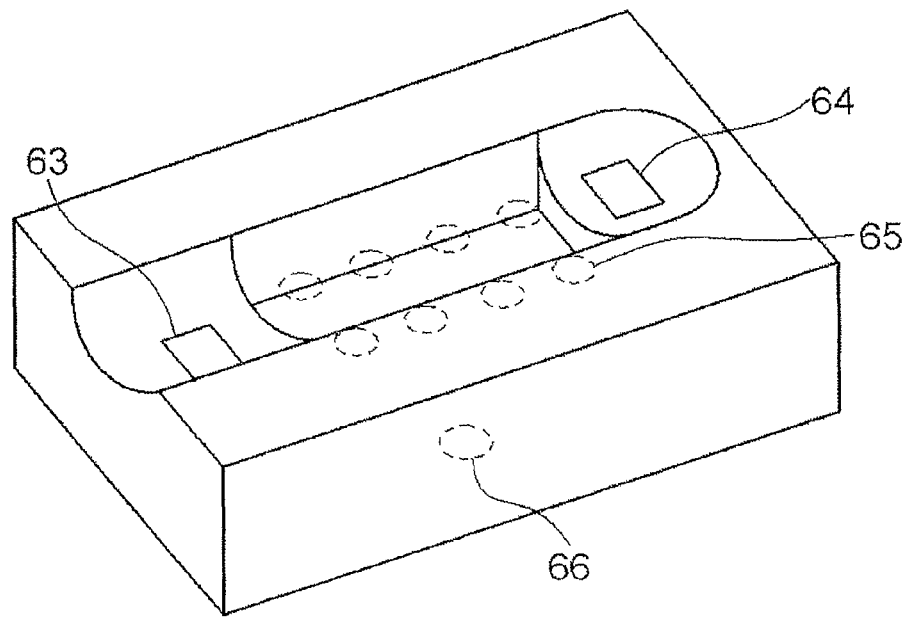
FIG. 6B is a diagram for describing the sensing unit of the biometric authentication device according to the second exemplary embodiment.

FIGS. 6A and 6B each show an external view of a sensing unit of the biometric authentication device. This device further includes a light source 65 to image the pattern of the finger and a camera 66 to image the pattern of the finger in addition to the devices in the first exemplary embodiment. According to such a configuration, the signal pattern (response signal) and the pattern of the finger can be captured substantially at the same time.

Figure 7:
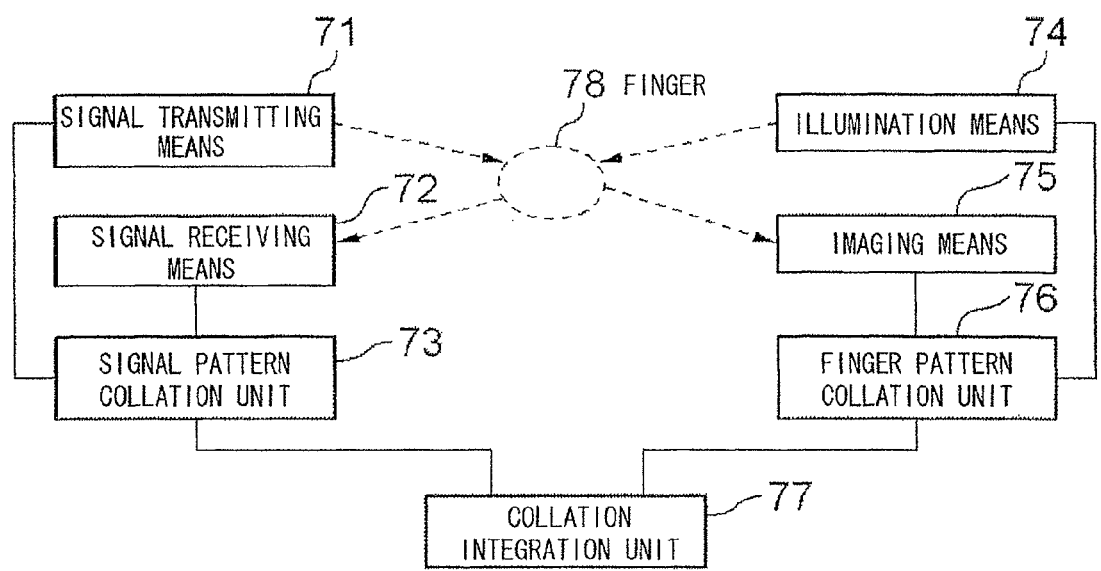
FIG. 7 is a diagram for describing a configuration of the biometric authentication device according to the second exemplary embodiment.

As shown in FIG. 7, the biometric authentication device includes a signal transmitting means 71 and a signal receiving means 72 that transmits and receives signals to and from the finger, as is similar to the first exemplary embodiment, a signal pattern collation unit 73 that performs collation based on the signal pattern that is obtained (response signal) and outputs the collation result, an illumination means 74 which is a light source to irradiate the finger with illumination light, an imaging means 75 which is a camera imaging the pattern of the finger, a finger pattern collation unit 76 that performs collation based on the finger pattern that is obtained and outputs the collation result, and a collation integration unit 77 that integrally outputs the collation result based on the collation result from the signal pattern collation unit 73 and the collation result from the finger pattern collation unit 76.

Note that the illumination means 74, the imaging means 75, and the finger pattern collation unit 76 constitute a finger pattern authenticating means.

Similarly to the first exemplary embodiment, the signal transmitting means 71, the signal receiving means 72, and the signal pattern collation unit 73 transmit the signal to the finger, receives the response signal from the finger, calculates the transfer function based on the signal pattern of the transmitted signal and the received response signal, performs collation using the feature amount based on the transfer function, calculates the distance value dsignal, and outputs the collation result Ssingal by threshold processing. The signal pattern collation unit 73 includes, as is similar to the first exemplary embodiment, a signal pattern generating means 11, a transfer feature calculating means 14, a feature amount extracting means 15, a feature amount storing means 16, and a feature amount collating means 17.

In this example, collation of the finger pattern is performed using the pattern of the finger such as blood vessel image. The technique of imaging the blood vessel of the finger and performing collation is disclosed, for example, in Japanese Unexamined Patent Application Publication No. 7-21373, Japanese Unexamined Patent Application Publication No. 10-127609, and the specification of Japanese Patent Application No. 2007-113264 by the applicant of the present invention.

[Patent document 4]

Japanese Unexamined Patent Application Publication No. 7-21373

[Patent document 5]

Japanese Unexamined Patent Application Publication No. 10-127609

[Patent document 6]

Specification of Japanese Patent Application No. 2007-113264

The illumination means 74 includes a near-infrared LED (Light Emitting Diode), and irradiates a second finger joint of the finger with near-infrared light. The wavelength of the near-infrared light may be about from 700 to 900 nm. In this example, near-infrared light having the wavelength of 850 nm is used. The illumination means 74 includes, as shown in FIGS. 6A and 6B, eight LEDs, four of which being arranged in left and the rest being arranged in right, so as to irradiate the medial finger portion of the finger uniformly (evenly).

The imaging means 75 images the pattern of the finger using a near-infrared camera. The near-infrared camera is equipped with a visible light cut-off filter that allows wavelength of 850 nm to transmit and interrupts disturbance light such as visible light. According to such a configuration, the pattern of the finger can be imaged.

In this biometric authentication device, as shown in FIGS. 6A and 6B, the LEDs are arranged in the same side as the camera with respect to the arrangement of the finger. Hence, the pattern that includes the blood vessel image which is the pattern inside the finger and skin surface pattern which is the pattern of the surface structure of the finger (fingerprint or joint line) can be imaged by the reflected light.

The finger pattern collation unit 76 performs DP matching (Dynamic Programming matching) on the obtained pattern of the finger using the feature amount (amount that indicates the pattern of the finger) based on the frequency spectrum, as disclosed in the patent document 6. Accordingly, collation is performed (collate the amount that indicates the pattern of the finger imaged (input) by the imaging means 75 with the amount that indicates the pattern of the finger that is stored in advance) to calculate the similarity dfinger, and the collation result Sfinger is output by threshold processing.

The collation integration unit 77 outputs end collation result Sfinal based on the collation result Ssignal and the collation result Sfinger.

When the user is authenticated as an authorized user only when both collation results are judged to be matched (coincident), logical AND of the collation results is output as the end collation result Sfinal. Calculating logical AND means the authentication by the signal pattern and the authentication by the finger pattern need to be satisfied at the same time; therefore, for example, attack by a fake finger is extremely difficult.

When the user is authenticated as an authorized user when at least one of the both collation results is judged to be matched, logical OR of the collation results is output as the end collation result Sfinal. False Rejection Rate and Correct Rejection Rate of the authentication using the signal pattern are denoted by FRRsignal and FARsignal, respectively, and False Rejection Rate and Correct Rejection Rate of the authentication using the finger pattern are denoted by FRRfinger and FARfinger, respectively. False Rejection Rate FRRfinal and Correct Rejection Rate FARfinal according to the logical OR can be expressed as the following expression (5) if each authentication is assumed to be performed independently.

$$FRR_{final} = FRR_{signal} FRR_{finger} \qquad (5)$$

$$FAR_{final} = 1 - (1 - FAR_{signal})(1 - FAR_{finger})$$

$$= FAR_{signal} + FAR_{finger} - FAR_{signal} FAR_{finger}$$

For example, assume that FARsignal is designed to satisfy FARsignal=FARfinger=$10^{-4}$. In this case, if FRRsignal=$5 \times 10^{-2}$ and FRRfinger=$1 \times 10^{-2}$, FRRfinal=$5 \times 10^{-4}$ and FARfinal☐$2 \times 10^{-4}$ are obtained.

Further, assume that FARsignal and FARfinger are designed to satisfy FARsignal=$10^{-5}$ and FARfinger=$10^{-4}$. In this case, if FRRsignal=$20 \times 10^{-2}$ and FRRfinger=$1 \times 10^{-2}$, FRRfinal=$2 \times 10^{-3}$ and FARfinal☐$1.1 \times 10^{-4}$ are obtained.

In this way, even when the same Correct Rejection Rate is set, the False Rejection Rate can be dramatically reduced.

The hypothesis that the characteristics of the transfer feature of the signal and the pattern of the finger are independent is almost verified. However, in reality, false rejection that is dependent on the way to put the finger has correlation. Although the accuracy is somewhat degraded compared with the ideal value, it is still greatly enhanced.

Although the collation integration unit 77 is configured to receive the collation results (Ssignal, Sfinger) after the threshold determination, it may be configured to receive the collation scores (distance value dsignal, similarity dfinger). In this case, the collation integration unit 77 is configured to calculate the integrated collation score dfinal using the two collation scores to perform collation determination using the collation score dfinal. The collation score dfinal is calculated by the following expression (6). Now, θ represents a parameter, and is experimentally obtained.

$$d_{final} = d_{signal} \cos\theta + d_{finger} \sin\theta \qquad (6)$$

While the sensing unit shown in FIG. 6B is configured to use the near-infrared light of 850 nm in the second exemplary embodiment, it may be configured to use the visible light of 450 nm. In this case, a blue LED is preferably used as an LED. Further, the transmission filter is preferably configured so as to allow the camera to perform sensing with the wavelength of 450 nm. Accordingly, the image in which the surface pattern of the finger (fingerprint, joint line, and so on) is emphasized can be taken.

Also in this case, the authentication of the finger can be performed by the substantially similar processing. In this case, collation may be performed using a collation method by minutiae of a fingerprint disclosed in a patent document 7 and the like as the finger pattern collation unit instead of performing DP matching using a frequency spectrum. It is known that fingerprints do not change dramatically unless a user is injured in a finger. Hence, a robust biometric authentication device can be provided that is capable of keeping the high accuracy against deterioration with age.

[Patent document 7]
Japanese Unexamined Patent Application Publication No. 59-000778

Although the LEDs are arranged in the same side as the camera in the sensing unit shown in FIG. 6B in the second exemplary embodiment, the LEDs may be arranged in the side opposite to the camera. In this case, the camera takes the blood vessel image by transmission light. The contrast of the blood vessel image which is the pattern inside the finger becomes larger in the transmitted light sensing. Therefore, the blood vessel pattern can be imaged more clearly. In this case as well, the authentication of the finger pattern can be carried out using the similar processing. Using the blood vessel image provides the biometric authentication device having higher tolerance to counterfeiting.

<Third Exemplary Embodiment>
(Application for Portable Telephones)

A portable telephone (portable telephone equipment, portable telephone terminal) according to a third exemplary embodiment includes a biometric authentication device based on a transfer feature described in the first exemplary embodiment. This portable telephone employs the biometric authentication to set (achieve a lock function) the state of the portable telephone from the state in which at least a part of function (in this example, function for achieving telephone conversation) of the portable telephone cannot be used (locked state) to the state in which the function can be used (unlocked state).

Figure 8:
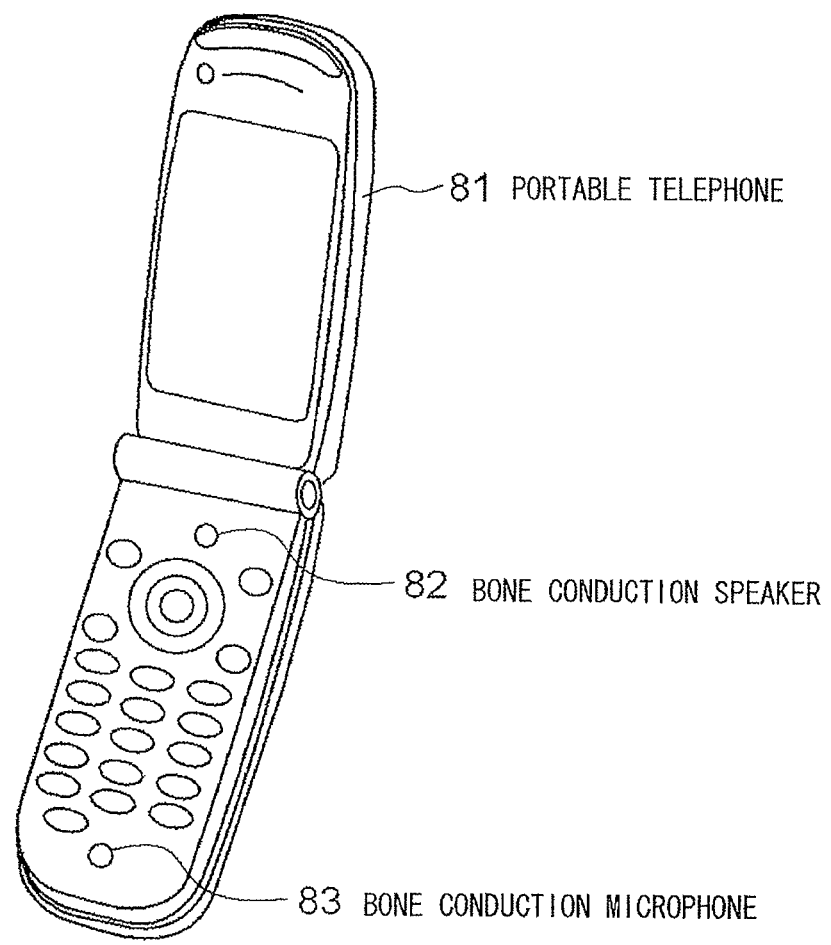
FIG. 8 is a diagram for describing a portable telephone equipped with a biometric authentication function according to a third exemplary embodiment.

As shown in FIG. 8, a portable telephone 81 according to the third exemplary embodiment includes a bone conduction speaker 82 as a signal generating means (signal transmitting means) 12, and a bone conduction microphone 83 as a signal receiving means 13. In this example, the bone conduction microphone and the bone conduction speaker are commonly used for telephone conversation. The portable telephone may additionally include a microphone and a speaker for telephone conversation.

Figure 9A:
FIG. 9A is a diagram showing a state in which the portable telephone equipped with the biometric authentication function according to the third exemplary embodiment contacts a head.
Figure 9B:
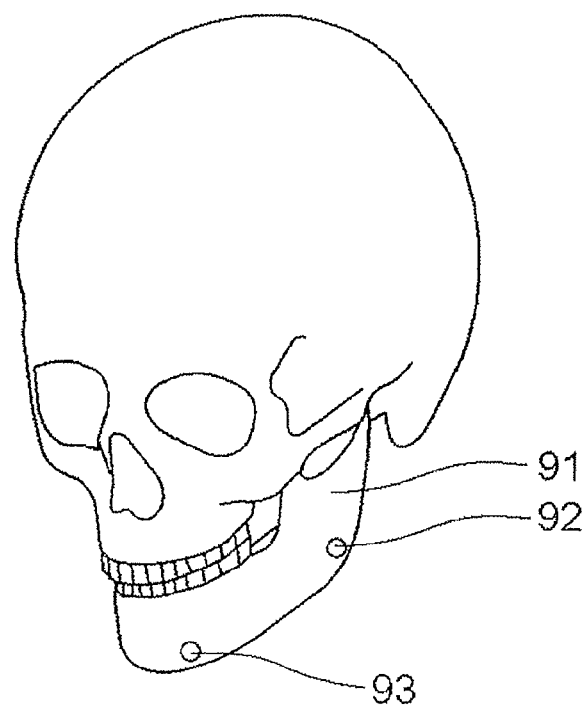
FIG. 9B is a diagram for describing a transmission point and a reception point when the portable telephone equipped with the biometric authentication function according to the third exemplary embodiment contacts the head.

In this example, as shown in FIGS. 9A and 9B, the portable telephone 81 contacts a head, to perform authentication based on the transfer feature in a mandible 91 using a point 92 on the mandible 91 as a signal transmission point and a point 93 as a signal reception point. The portable telephone 81 may be configured to perform authentication by a user putting a finger thereon.

Figure 10:
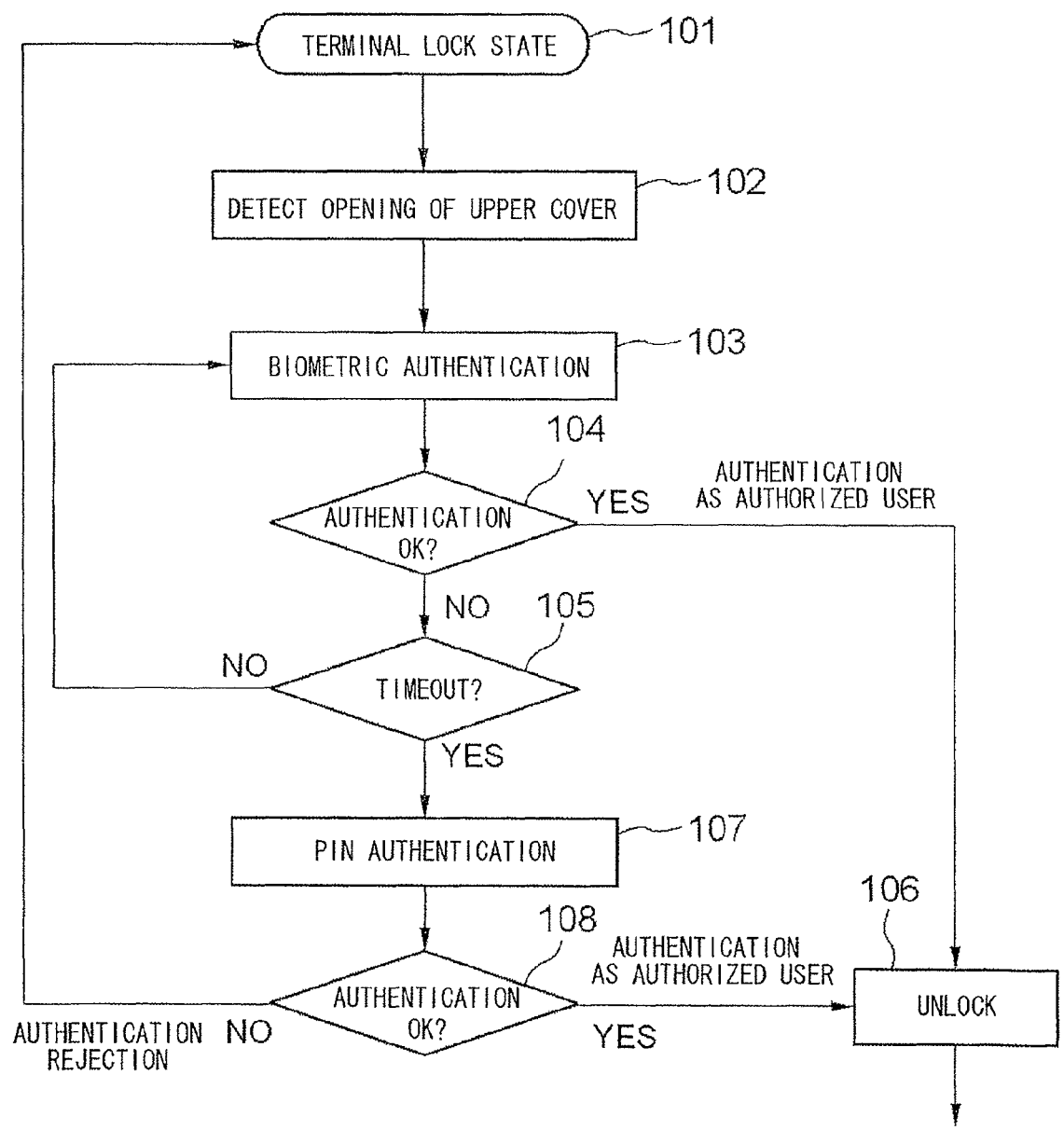
FIG. 10 is a diagram for describing the operation of a control unit of the portable telephone equipped with the biometric authentication function according to the third exemplary embodiment.

FIG. 10 is a diagram for describing the operation of the control unit in a folding-type portable telephone. The third exemplary embodiment applies the biometric authentication to the lock function of the terminal. The user of the terminal enrolls a finger (for example, forefinger of the right hand), or a mandible part (for example, left side of the lower jaw part), or both of them in the portable telephone 81 in advance according to predetermined enrollment processing. In this example, description will be made of a case in which both data are enrolled.

When multiple data is enrolled, the portable telephone 81 collates each of the data of the finger and the lower jaw that are enrolled with the data in the query side that is input. When any of the data matches, the portable telephone 81 determines that the authentication is made (authentication is successfully completed (established)).

When the terminal is folded and the portable telephone 81 is not used, the control unit sets the terminal to the locked state (step 101). When using the portable telephone 81, the user operates the terminal so that the state of the terminal is changed from the state in which the terminal is folded to the state in which the upper cover is opened (opening state).

The control unit detects that the state of the terminal becomes the opening state (step 102). When detecting the opening state, the control unit carries out the above-described biometric authentication of transmission, reception, and collation of the signal (step 103). The control unit determines if the authentication is successfully completed (step 104). When the authentication is successfully completed, the control unit sets the state of the terminal to the state of unlock (step 106). Accordingly, the telephone conversation function of the terminal is available.

When the authentication is failed, the control unit determines whether a predetermined time has passed after the terminal becomes the opening state (timeout occurs) (step 105). When timeout does not occur, the control unit restarts the biometric authentication; when timeout occurs, the control unit performs authentication (PIN authentication) by a personal identification number (PIN) (step 107). The control unit determines whether to keep the state of the terminal locked or to release the lock based on the personal identification number that is received (step 108).

By the way, it takes certain period of time from when the user opens the upper cover to when the user puts his/her finger on the terminal or puts the terminal on the lower jaw. Thus, as described above, during the time from when the terminal becomes the opening state to when the predetermined time passes, the biometric authentication is repeatedly performed.

Further, the control unit may be configured to forcibly get out of the loops of the biometric authentication (steps 103~104~105) to transit to the PIN authentication when a cancel button is pushed.

By the way, when the personal identification number authentication, the face authentication, or the fingerprint authentication or the like is used, certain period of time is required for the operation of inputting the personal identification number, the operation of turning the face toward the camera, or scanning the finger by a line sensor. On the other hand, in the case of an incoming call, the lock needs to be promptly released. Hence, the portable telephone with which related face authentication function, fingerprint authentication function or personal identification number authentication function is equipped is configured so that the telephone conversation function is available in the case of an incoming call by only pushing the receiving button without releasing the lock.

Meanwhile, with the portable telephone according to the third exemplary embodiment, in the case of an incoming call, biometric authentication may be performed when a user opens the upper cover, pushes the receiving button, and puts the terminal on his/her lower jaw. In short, the biometric authentication can be performed during the same operation by the user as the related terminal in the case of an incoming call.

Alternatively, the operation of pushing the receiving button may be omitted since personal authentication in the case of an incoming call means that the user is willing to receive a call. Specifically, regardless of whether the terminal is locked or unlocked, the portable telephone may be operated to allow the user to start telephone conversation when the personal authentication is performed by biometric authentication in the case of an incoming call. This will enhance usability for the user.

When the portable telephone is used in the case of making a phone call, or as an information terminal function such as e-mail or WEB access instead of being used in an incoming call, the user tends to use a part of a finger than a part of the lower jaw part for the biometric authentication. Hence, in this case, the user may put a part of a finger on the portable telephone 81. For example, the user holds a case of the portable telephone 81 with his/her left hand and puts the forefinger of the right hand on the portable telephone 81. The portable telephone 81 thus performs personal authentication (biometric authentication) of the terminal. Accordingly, the user is able to smoothly perform the subsequent operations of searching an address book of the portable telephone 81 and operating e-mail.

<Fourth Exemplary Embodiment>
(Application for Portable Telephone Equipped With Non-Contact IC)

A portable telephone according to a fourth exemplary embodiment includes a function using a non-contact-type IC (non-contact IC function) that may be used for electronic money, for example.

A non-contact IC technique is widely used as electronic money (electronic payment), a commuter pass or a ticket of a train or a bus. This technique is standardized, and is disclosed in a non-patent document 3 and so on. A portable telephone with which the non-contact-type IC chip is equipped is widely spread as well.

[Non-patent document 3]
Japanese Standards Association, "Specification of implementation for IC cards—Part 4: High speed proximity cards", Jul. 20, 2005, JISX6319-4

A portable telephone is known that has a function (lock function) of setting the state of the portable telephone to the state in which the non-contact IC function can be used or the state in which the non-contact IC function cannot be used by using PIN authentication, or biometric authentication using fingerprint authentication or face authentication. However, a user hardly uses this lock function when using the non-contact IC function as electronic money or at a ticket gate.

The reason for this will be that the operation of inputting PIN, scanning a finger, or turning a face toward a camera is complicated, and usability is unsatisfactory (low).

The fourth exemplary embodiment applies the authentication technique using a signal pattern to the portable telephone with which the non-contact IC function is equipped, to enhance usability in unlocking.

Figure 11:
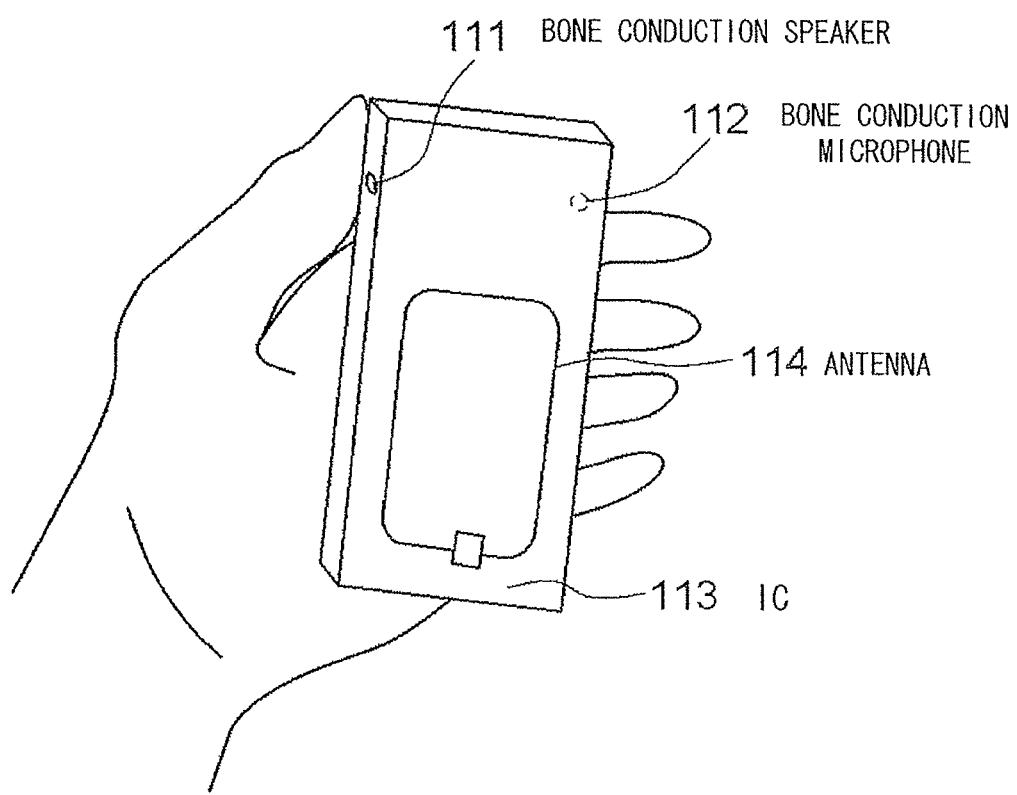
FIG. 11 is a diagram for describing a portable telephone equipped with a biometric authentication function according to a fourth exemplary embodiment.

As shown in FIG. 11, this portable telephone includes a bone conduction speaker 111, a bone conduction microphone 112, an IC 113 to implement a non-contact IC function, and an antenna 114 to carry out non-contact communication.

The antenna 114 is typically arranged in a bottom surface of a portable telephone, and is arranged and used substantially parallel to a device in a reader side of the non-contact IC card. The bone conduction speaker 111 and the bone conduction microphone 112 are arranged in a side of the case of the portable telephone. Accordingly, when the user uses the non-contact IC function, the user puts his/her finger on the bone conduction speaker 111 and the bone conduction microphone 112, to easily hold a case of a portable telephone.

The bone conduction speaker is arranged on the push button switch. According to such a configuration, the portable telephone is able to detect the operation of the finger pushing the push button switch.

Figure 12:
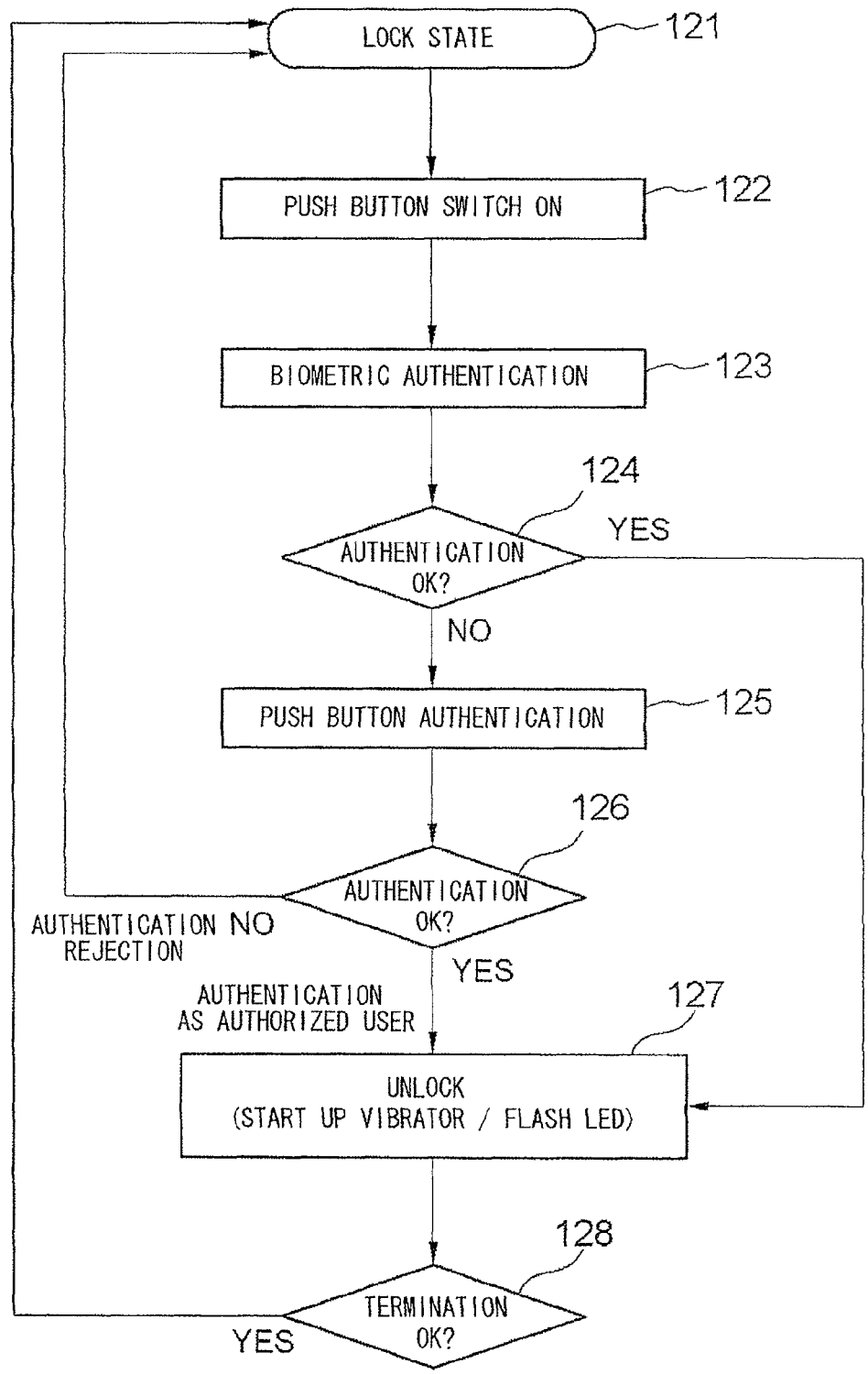
FIG. 12 is a diagram for describing the operation of a control unit of the portable telephone equipped with the biometric authentication function according to the fourth exemplary embodiment.

FIG. 12 is a diagram for describing the operation of the control unit of the portable telephone that is equipped with the biometric authentication function according to the fourth exemplary embodiment. When the user desires to set the state of the portable telephone to the state in which the non-contact IC function is available (desires to release the lock of the non-contact IC function), the user first pushes the push button switch in which the bone conduction speaker is arranged. Accordingly, the control unit of the portable telephone detects that the push button switch is pushed (turned ON) (step 122).

The control unit then starts the biometric authentication in the similar way as in the third exemplary embodiment (step 123). The control unit releases the lock of the non-contact IC function when authentication is successfully completed (step 127), and carries out the next push button authentication when the authentication is failed (step 125). The push button authentication here means the authentication using ON or OFF of the push button switch. The push button authentication converts long-short of ON time to the letter string based on the Morse code, and determines whether the letter string matches the letter string which is enrolled in advance.

For example, when a letter string "SOS" is enrolled, a user pushes the push button switch so that ON time is "short-short-short-long-long-long-short-short-short" to input the signal obtained by Morse coding the letter string "SOS". The control unit converts the input signal to the letter string based on the Morse code, and determines that the authentication is successfully completed when the letter string matches the letter string which is enrolled in advance.

The control unit may be configured to perform authentication based on a bit string that simply indicates two states instead of the Morse code. In this case, the control unit stores, for example, "short-short-short-long-long-long-short-short-short" (bit string of long-short) in advance, and determines that the authentication is successfully completed when the push button switch is pushed so that the ON time is "short-short-short-long-long-long-short-short-short" in authentication.

When combination of "long" and "short" is used, a user may memorize the code for unlocking by coding " short-short-long-short-short-long", for example, in accordance with the rhythm of a music that the user knows well, instead of memorizing the code by letters. Therefore, the user can easily memorize the authentication code without using the code as the Morse code which is not generally used.

Instead of using two states of long and short of the push button, three states of short, long, and no may be combined for coding.

Note that the push button authentication 125 may be performed in parallel (concurrently and independently) with the biometric authentication 123. In this case, it is preferable that the push button authentication is performed including the operation (122) of pushing the button for the first time when ON of the push button switch is detected (122) in the signal string of the push button. Hence, the number of times the user pushes the button is reduced by once, thereby enhancing usability.

Further, the control unit may be configured to carry out the biometric authentication every time the operation of pushing the button is performed in push button authentication.

When the push button authentication 125 and the biometric authentication 123 are operated in parallel as stated above, the control unit is preferably configured to release the lock when the authentication is successfully completed by the biometric authentication even before the push button authentication is successfully completed (before determination is made whether the authentication is successfully completed). Accordingly, the user can interrupt the operation of the push button authentication after the completion of the authentication.

When the personal authentication is performed and the lock is released, the control unit starts up a vibrator and flashes the LEDs (step 127). Accordingly, the user can recognize that the lock is released. As a result, since the user can promptly determine (recognize) whether the IC function can be available, the next operation of the user can be promptly determined (whether to continue the operation of pushing the push button in the push button authentication or to hold the portable telephone over the IC reader).

When the usage of the non-contact IC function is successfully completed or a predetermined time is passed, the control unit determines that the usage of the non-contact IC function is terminated (step 128), and sets the state of the portable telephone to the state (locked state) in which the non-contact IC function cannot be used (step 121).

The control unit may be configured to allow a user to release the lock using PIN authentication or the like when the person to be authenticated is refused due to the failure of authentication by biometric authentication and push button authentication although the person to be authenticated should be authorized.

Note that the present invention is not limited to the exemplary embodiments described above but can employ various types of modified examples within the scope of the present invention.

This application claims the benefit of priority, and incorporates herein by reference in its entirety, the following Japanese Patent Application No. 2008-40882 filed on Feb. 22, 2008.

INDUSTRIAL APPLICABILITY

The present invention is applicable to a biometric authentication device using an acoustic signal or an electrical signal. Further, the present invention is also applicable to a portable telephone including the biometric authentication device.

The invention claimed is:

1. A biometric authentication device comprising:
a signal pattern generating unit that generates a signal pattern of a signal transmitted to a living body;
a signal transmitting unit that transmits a signal to the living body based on the signal pattern from the signal pattern generating unit;
a signal receiving unit that receives a response signal transmitted from the living body, the received response signal being in response to the transmitted signal that is based on the generated signal pattern;
a transfer feature calculating unit that calculates a transfer feature of a signal transmitted through the living body based on the signal pattern from the signal pattern generating unit and the response signal received by the signal receiving unit;
a feature amount extracting unit that extracts a feature amount based on the transfer feature that is calculated, the feature amount varying for every living body; and
a feature amount collating unit that collates the extracted feature amount with a feature amount stored in a feature amount storing unit in advance, wherein
the signal pattern generating unit is configured to change the signal pattern every time the signal pattern generating unit generates the signal pattern.

2. The biometric authentication device according to claim 1, wherein
the signal transmitting unit is configured to transmit the signal to the living body while being contacted to the living body, and
the signal receiving unit is configured to receive the response signal from the living body while being contacted to the living body.

3. The biometric authentication device according to claim 1, wherein
the signal transmitting unit is configured to transmit the signal through a bone conduction-type speaker,
the signal receiving unit is configured to receive the response signal through a bone conduction-type microphone, and
the transfer feature is an acoustic transfer function in the living body.

4. The biometric authentication device according to claim 1, wherein
the signal transmitting unit is configured to transmit the signal through an electrode,
the signal receiving unit is configured to receive the response signal through an electrode, and
the transfer feature is an electrical transfer function in the living body.

5. The biometric authentication device according to claim 1, wherein the signal pattern generating unit is configured to generate a signal pattern indicating white noise as the signal pattern.

6. The biometric authentication device according to claim 1, wherein
the signal transmitting unit is configured to transmit the signal to a part of a finger in the living body,
the signal receiving unit is configured to receive the response signal from the part of the finger in the living body, and
the transfer feature is a transfer feature of the part of the finger.

7. The biometric authentication device according to claim 6, comprising a finger pattern authenticating unit that receives a pattern of a finger and collates an amount that indicates the input pattern of the finger with an amount that indicates a pattern of a finger that is stored in advance,
wherein the biometric authentication device is configured to perform the biometric authentication based on a collation result by the feature amount collating unit and a collation result by the finger pattern authenticating unit.

8. A portable telephone comprising the biometric authentication device according to claim 1, the portable telephone comprising:
a control unit that sets a state of the portable telephone to a state in which at least one function of the portable telephone can be used or a state in which at least one function of the portable telephone cannot be used based on the biometric authentication by the biometric authentication device.

9. The portable telephone according to claim 8, wherein the function includes a function that uses a non-contact-type IC.

10. A biometric authentication method comprising:
a signal pattern generating process that generates a signal pattern of a signal transmitted to a living body;

a signal transmitting process that transmits a signal to the living body based on the signal pattern generated by the signal pattern generating process;

a signal receiving process that receives a response signal transmitted from the living body, the received response signal being in response to the transmitted signal that is based on the generated signal pattern;

a transfer feature calculating process that calculates a transfer feature of a signal transmitted through the living body based on the signal pattern generated by the signal pattern generating process and the response signal received by the signal receiving process;

a feature extracting process that extracts a feature amount based on the transfer feature that is calculated, the feature amount varying for every living body; and a feature amount collating process that collates the extracted feature amount with a feature amount stored in a feature amount storing unit in advance, wherein the signal pattern is changed every time the signal pattern is generated in the signal pattern generating process.

11. The biometric authentication method according to claim 10, wherein the signal transmitting process is configured to transmit the signal to the living body while being contacted to the living body, and the signal receiving process is configured to receive the response signal from the living body while being contacted to the living body.

12. The biometric authentication method according to claim 10, wherein the signal transmitting process is configured to transmit the signal through a bone conduction-type speaker, the signal receiving process is configured to receive the response signal through a bone conduction-type microphone, and the transfer feature is an acoustic transfer function in the living body.

13. The biometric authentication method according to claim 10, wherein the signal transmitting process is configured to transmit the signal through an electrode, the signal receiving process is configured to receive the response signal through an electrode, and the transfer feature is an electrical transfer function in the living body.

14. The biometric authentication method according to claim 10, wherein the signal pattern generating process is configured to generate a signal pattern indicating white noise as the signal pattern.

15. A storage medium that stores a biometric authentication program making a biometric authentication device comprising a signal transmitting unit that transmits a signal to a living body and a signal receiving unit that receives a response signal transmitted through the living body to perform biometric authentication based on the response signal achieve the following:

a signal pattern generating unit that generates a signal pattern of a signal transmitted to the living body and outputs the signal pattern that is generated to the signal transmitting unit;

a transfer feature calculating unit that calculates a transfer feature of a signal transmitted through the living body based on the signal pattern from the signal pattern generating unit and the response signal received by the signal receiving unit;

a feature amount extracting unit that extracts a feature amount based on the transfer feature that is calculated, the feature amount varying for every living body; and a feature amount collating unit that collates the extracted feature amount with a feature amount stored in a feature amount storing unit in advance, wherein the signal pattern generating unit achieves change of the signal pattern every time the signal pattern generating unit generates the signal pattern, and wherein the received response signal is in response to the transmitted signal.

\* \* \* \* \*